United States Patent
Falwell

(10) Patent No.: US 6,464,698 B1
(45) Date of Patent: Oct. 15, 2002

(54) MEDICAL DEVICE HAVING AN INCREMENTALLY DISPLACEABLE ELECTRODE

(75) Inventor: Gary S. Falwell, Manchester, NH (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/453,732

(22) Filed: Dec. 2, 1999

(51) Int. Cl.⁷ .............................................. A61B 18/14
(52) U.S. Cl. ........................................ 606/41; 607/99
(58) Field of Search ........................... 606/41, 42, 45, 606/46, 49; 607/99, 113, 122

(56) References Cited

U.S. PATENT DOCUMENTS

| | | | |
|---|---|---|---|
| 5,458,597 A | * 10/1995 | Edwards et al. | 606/41 |
| 5,482,037 A | 1/1996 | Borghi | 128/642 |
| 5,885,278 A | 3/1999 | Fleischman | 128/642 |
| 6,010,500 A | 1/2000 | Sherman et al. | 606/41 |
| 6,113,591 A | 9/2000 | Whayne et al. | 606/34 |
| 6,178,354 B1 * | 1/2001 | Gibson | 607/116 |

FOREIGN PATENT DOCUMENTS

WO        97/42893    * 11/1997   ............ 606/41

* cited by examiner

Primary Examiner—Lee Cohen
(74) Attorney, Agent, or Firm—Darby & Darby

(57) ABSTRACT

A medical device in one embodiment includes an electrode which is connected to a flexible, tubular, movable member, such as a catheter shaft or an outer sheath, which is slidably extended over a guide wire, flexible shaft, or other tubular member. A displacement mechanism is connected to the movable member, and may be actuated one or more times to displace the movable member in successive, predetermined increments, for creating a linear lesion or for performing diagnostic functions.

10 Claims, 2 Drawing Sheets

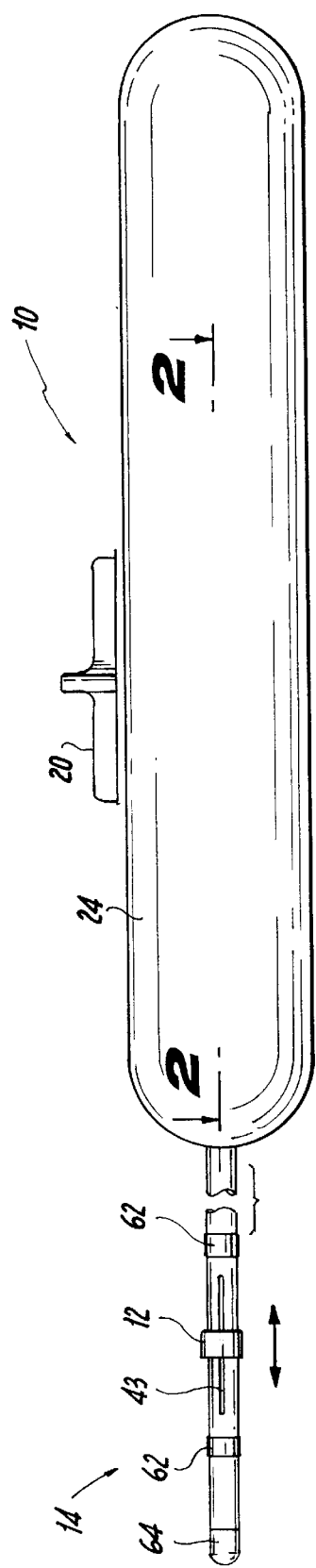
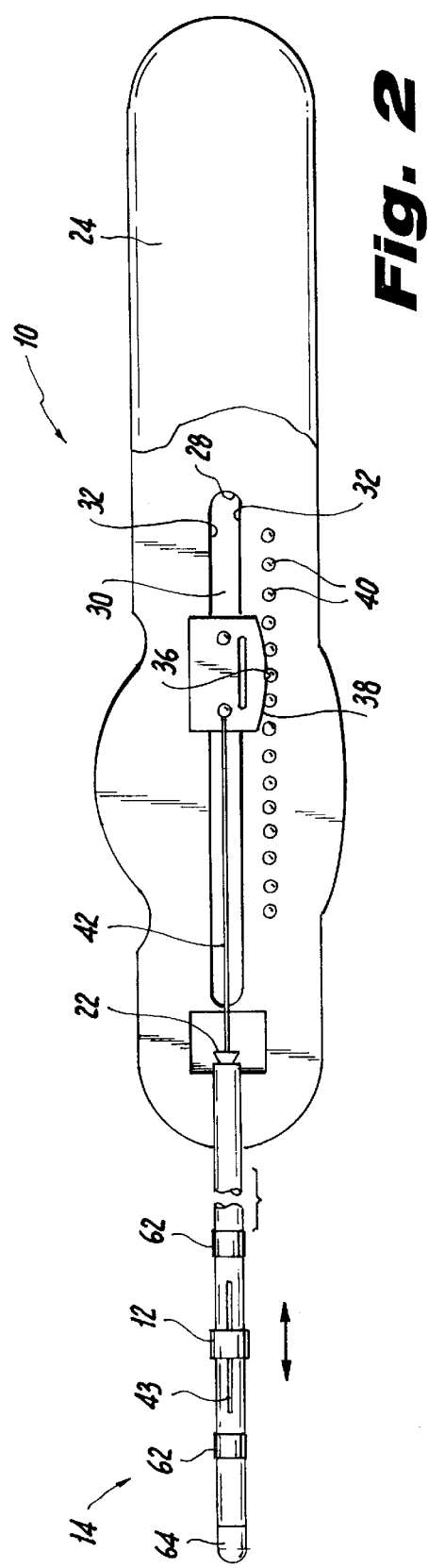

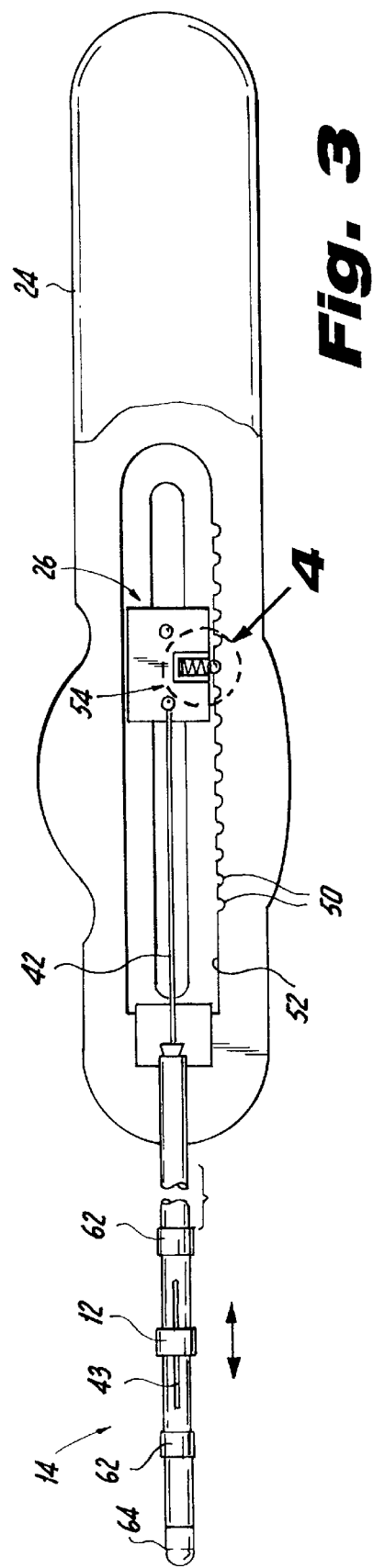
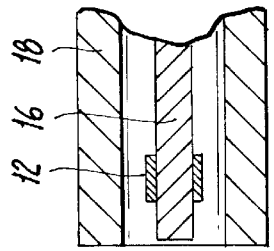

MEDICAL DEVICE HAVING AN INCREMENTALLY DISPLACEABLE ELECTRODE

FIELD OF THE INVENTION

This invention relates to medical devices for performing diagnostic, mapping, ablative, and other procedures and, more particularly, to a medical device for incrementally moving an electrode a predetermined distance upon each actuation of the device.

BACKGROUND OF THE INVENTION

The human heart is a very complex organ, which relies on both muscle contraction and electrical impulses to properly function. The electrical impulses travel through the heart walls, first through the atria, and then through the ventricles, with those impulses causing the corresponding muscle tissue in the atria and ventricles to contract. Thus, the atria contract first, followed by the ventricles. This order is essential for proper functioning of the heart.

Over time, the electrical impulses traveling through the heart can begin to travel in improper directions, thereby causing the heart chambers to contract at improper times. Such a condition is generally termed a cardiac arrhythmia, and can take many different forms. When the chambers contract at improper times, the amount of blood pumped by the heart decreases, which can result in premature death of the person.

Non-surgical procedures, for example, management with drugs, are favored in the treatment of cardiac arrhythmias. However, some arrhythmias are not treatable with drugs. For example, drug therapy to combat certain types of cardiac arrhythmias has been found to be successful in only 30 to 50 percent of patients. Because of this low success rate, another conventional remedy is to perform a surgical procedure. According to these procedures, various incisions are made in the heart to block conduction pathways in an effort to abolish the arrhythmia.

More recently, minimally invasive techniques have been developed which are used to locate cardiac regions responsible for the cardiac arrhythmia and to disable the short-circuit function of these areas. According to these techniques, electrical energy is applied to a portion of the heart tissue to ablate that tissue and produce scars which interrupt the reentrant conduction pathways. The regions to be ablated are typically first determined by endocardial mapping techniques. Mapping involves percutaneously introducing a catheter having one or more electrodes into the patient, passing the catheter through a blood vessel (e.g. the femoral vein or aorta) and into an endocardial site (e.g., the atrium or ventricle of the heart), and inducing a tachycardia so that a continuous, simultaneous recording can be made with a multichannel recorder at each of several different endocardial positions. When a tachycardia focus is located, as indicated in the electrocardiogram recording, its position is marked so that cardiac arrhythmias at the located site can be ablated. An ablation catheter with one or more electrodes can then transmit electrical energy to the tissue adjacent the electrode to create a lesion in the tissue. One or more suitably positioned lesions will typically create a region of necrotic tissue which serves to disable the propagation to the errant impulse caused by the tachycardia focus.

Ablation is carried out by applying energy to the catheter electrodes once the electrodes are in contact with the cardiac tissue. The energy can be, for example, RF, DC, ultrasound, microwave, or laser radiation. When RF energy is delivered between the distal tip of a standard electrode catheter and a backplate, there is a localized RF heating effect. This creates a well-defined, discrete lesion slightly larger than the surface area of the electrode (i.e., the "damage range" for the electrode), and also causes the temperature of the tissue in contact with the electrode to rise.

It has been found that to overcome certain cardiac arrhythmias, it is often necessary to create a relatively long, continuous lesion (i.e., a linear lesion) in the patient's heart tissue. Conventional techniques include applying multiple point sources in an effort to create a long and continuous lesion. Such a technique is relatively involved, and requires significant skill and attention from the clinician performing the procedure.

Another conventional ablation procedure for creating linear lesions is commonly referred to as a "drag" method. According to that method, an ablation catheter carrying one or more ablation electrodes is manipulated through a patient's blood vessels and to a desired location within the patient's heart. One or more of the electrodes is manipulated into contact with the heart tissue. Ablation energy is then delivered through the electrode(s) and into the tissue to create a lesion, which is typically slightly larger than the surface area of the electrode contacting the tissue (the electrode's damage range). After the electrode has been disposed in that location for a sufficient time to ablate the adjacent tissue, the clinician then manually moves the catheter a selected amount by pulling on the catheter shaft, and ablation energy is again delivered to the electrode(s) to ablate the tissue that is then adjacent to the electrode. By continuing this procedure, the clinician attempts to create a continuous, linear lesion to block an aberrant pathway.

However, to create a continuous lesion, the clinician must be careful not to move the catheter too far between successive ablations. If the clinician should accidentally move the catheter too far, then the lesion created will not be continuous, and the aberrant pathway may not be destroyed, requiring that the patient undergo yet another surgical procedure.

Accordingly, it will be apparent that there continues to be a need for a device for performing ablations which ensures the creation of linear lesions, by automatically displacing an ablation electrode in successive, incremental, movements of a predetermined, known distance. In addition, the need exists for a device which moves an electrode in known increments for use in performing other medical procedures. The instant invention addresses these needs.

SUMMARY OF THE INVENTION

According to one aspect of the invention, an electrode is slidably mounted over a tubular shaft, for example, a catheter shaft. The electrode is connected to one end of a displacement member, such as a mandrel, stiff wire, or the like. The displacement member may extend through the inside of the catheter shaft and connect to the electrode through a slot formed in the shaft, or may extend along the outside of the catheter shaft to connect to one end of the electrode. The displacement member includes a second end that is connected to a control mechanism which may be manipulated by a user to advance and/or retract the displacement member in controlled, known increments. In this manner, the electrode is incrementally displaced in successive, predetermined distances, and is suitable for use in ablative procedures to create long, continuous lesions.

Thus, in one illustrative embodiment, the present invention is directed to a medical device comprising an elongated, tubular shaft, an electrode slidably mounted over the shaft, an elongated displacement member connected to the electrode, and a control mechanism connected to the displacement member and operative to displace the displacement member in predetermined, incremental amounts to displace the electrode in the incremental amounts.

In another illustrative embodiment, the invention is directed to a method of performing a medical procedure, comprising the following steps: positioning an ablation electrode at a selected site within a patient, the ablation electrode having predetermined dimensions; delivering ablation energy to the electrode to ablate the patient's tissue disposed adjacent to the tissue; displacing the electrode a predetermined increment, wherein the predetermined increment is determined based upon one or more of the dimensions of the electrode; and repeating the above steps one or more times to create a continuous lesion.

DESCRIPTION OF THE DRAWINGS

Other objects, features and advantages of the invention discussed in the above summary of the invention will be more clearly understood from the following detailed description of preferred embodiments, which are illustrative only, when taken together with the accompanying drawings in which:

FIG. 1 is a side view of a medical device incorporating a mechanism for displacing an electrode in predetermined increments, the medical device illustrating one embodiment of the present invention;

FIG. 2 is a cross-sectional view taken along the line 2—2 of FIG. 1;

FIG. 3 is a cross-sectional view similar to FIG. 2 and showing another illustrative embodiment of the present invention;

FIG. 4 is an enlarged sectional view taken of the area 4 of FIG. 3; and

FIG. 5 is a cross-sectional view of another embodiment of the present invention.

DETAILED DESCRIPTION OF THE PREFERRED EMBODIMENTS

Referring now to FIG. 1, there is shown a mechanism 10 for incrementally displacing an electrode 12 according to one illustrative embodiment of the invention. In one illustrative embodiment, the electrode 12 is slidably extended over an elongated, tubular member 14, for example, a catheter shaft or the like. An incremental displacement mechanism, generally designated 20, is connected to the electrode and is operative, upon each actuation thereof, to displace the electrode a predetermined distance relative to the tubular member 14. Thus, for example, in an ablation procedure, the device 10 may be manipulated through a patient's blood vessels until the electrode 12 is disposed in a desired location, such as in contact with an "active site" in the heart. Ablation energy is delivered to the electrode to destroy the adjacent tissue. The clinician then actuates the displacement mechanism 20 to incrementally displace the electrode relative to the member 14. The procedure is continued to create a continuous lesion of a desired length.

Referring to FIG. 1, the tubular member 14 preferably comprises a conventional catheter shaft, which is flexible for manipulation through a patient's blood vessels and to a site of interest within a patient, for example, an active site. The catheter shaft defines an interior lumen 22 (as shown in FIG. 2), which in one embodiment is sized to allow for extension of a portion of the incremental displacement mechanism therethrough, as is described in greater detail below.

Alternatively, the electrode 12 may be mounted on a slidable inner tube 16 which is connected to the control mechanism 20 and therefore is slidably extended from and retracted into an outer sheath 18 (FIG. 5). In this manner, the entire inner tube 16 is advanced in predetermined increments, along with the electrode mounted on it.

The medical device 10 comprises a housing 24 which houses a portion of the catheter shaft 14 and the displacement mechanism 20 therein. Referring to FIGS. 2 and 3, one illustrative embodiment of the displacement mechanism 20 will be described. The displacement mechanism comprises a slider control member 26 which travels within a longitudinal track 28 formed in the housing 24. In one embodiment, the track is in the form of a longitudinal recess 30 and includes a pair of opposing, inwardly facing shoulders 32 spaced a selected distance above the recess 30. The slider control member 26 includes an enlarged base portion (not shown) which cooperates with the respective shoulders to prevent the slider control member from escaping from the track, while at the same time allowing the slider control member to slide along the track and thereby be displaced longitudinally along the housing 24.

The slider control member 26 and housing 24 include respective components of the incremental advancement mechanism 20 that is operative to advance the slider control member 26 in predetermined increments relative to the housing 24. In one embodiment, the slider control member includes a resilient, outwardly concave receptacle 36 formed in one side wall 38 of the member (FIG. 2) The housing is formed with a plurality of upstanding, spaced apart detent pins 40, with the spacing between adjacent pins serving to define the length of the increments. The side wall 38 is preferably formed of resilient material, so that the material flexes away from the pins as the slider control member is advanced past the pins, with the pins being received in the receptacle to releasably lock the slider control member in place relative to the housing 24. Because the side wall 38 is formed of resilient material, the slider control member may be advanced past the respective detent pins, with a portion of the side wall flexing away from the detent pins as the detent pins pass by. However, the size of the pins and spacing from the side wall 38 is preferably selected in such a manner that as the slider control member passes across the pins, each pin is received in the receptacle 36, with the sides of the receptacle resisting further movement of the captured pin. Such engagement requires that a predetermined amount of force be applied in a longitudinal direction to the slider control member 26 to overcome the engagement. In this manner, an operator is made aware when each pin is aligned with the receptacle and, therefore, the extent to which the slider control member has been advanced relative to the housing.

Preferably, the side wall 38 of the slider control member 26 is convex or otherwise curved to minimize the contact between the edges of the side wall and the adjacent pins 40 (FIG. 2). In this manner, displacement of the slider control member is impeded almost exclusively by the pin 40 engaged with the receptacle 36, such that it is clear to the operator when a pin engages the receptacle.

In one illustrative embodiment, the slider control member 26 is connected to a mandrel 42 which connects at its distal end to the slidable electrode 12. The mandrel may be a stiff wire or other suitable shaft to allow for either advancing or retracting the electrode, or alternatively may comprise a thin wire which is suitable for drawing the electrode proximally (i.e., away from the distal end of the medical device 10).

The medical device control handle 24 may take many different forms. One suitable form of control handle is disclosed in U.S. Pat. No. 5,462,527 to Stevens-Wright, the disclosure of which is hereby expressly incorporated by reference as if fully set forth herein. Any control handle is suitable for use in connection with the present invention, so long as the control handle includes a member which is slidable relative to the housing. Another suitable form of control handle is disclosed in U.S. Pat. No. 5,611,777 to Bowden et al., which is expressly incorporated herein by reference.

The mandrel 42 may be in the form of a shaft, stiff wire, hypotube, or the like, and extends distally from the slider control member 26 through the handle 24, through the lumen 22 formed inside of the shaft 14, and then extends laterally with respect to the catheter shaft through a slot 43 and :into engagement with the inside surface of the slidable electrode. Such a construction is disclosed in detail in U.S. patent application Ser. No. 09/203,922, and now U.S. Pat. No. 6,178,354, the disclosure of which is expressly incorporated herein by reference. Alternatively, the mandrel may extend from the slider control member through an opening in the handle, and then along the outer surface of the shaft and into engagement with the proximally facing edge of the sliding electrode 12.

Referring now to FIGS. 3 and 4, there is shown another illustrative embodiment of the present invention. In that embodiment, the engagement member of the incremental displacement assembly 20 is formed on the slider control member, while the receptacle is in the form of a plurality of spaced apart, concave detent grooves 50 formed on an inside wall 52 of the housing 24. The engagement member on the slider control member is preferably in the form of a ball plunger assembly 54 that includes a ball 56 contained within a cylinder 58 and which is biased to an outwardly disposed position by means of a spring 60 within the cylinder. Thus, as the slider control member is advanced along the track, the ball is biased into the respective detent grooves 50, with the operator then having to apply sufficient force to the member to overcome the spring bias and thereby clear the ball from the groove to advance the slider control member along the track.

As is well known to those skilled in the art, each electrode has a damage range, which is dependent on various factors, such as electrode length, type of ablating energy used, electrode thickness, and ,the like. Typically, the damage range for an electrode is slightly larger than the surface area of the electrode that is in contact with the tissue. Thus, the spacing between the detent grooves 50 (FIG. 3) or detent pins 40 (FIG. 2) is dependent on the damage range of the sliding electrode 12. Preferably, the distance between the grooves 50 or pins 40 is slightly longer than the axial length of the electrode to optimize an ablation procedure while still ensuring the creation of a continuous lesion.

While the invention has been described primarily in the context of ablative procedures, it will be understood by those skilled in the art that the invention may be used for diagnostic and other therapeutic functions. For example, the medical device 10 is particularly suitable for use in diagnostic applications, because the dynamically moveable electrode 12 offers the user a means for altering the distance between the electrode 12 and respective fixed electrodes 62 located at fixed locations along the shaft 14.

In operation, a site of interest is determined by positioning the distal portion of the medical device 10 in the heart and sensing the electrical signals using one or more of the electrodes 12 or 62, with the signals being transmitted to an appropriate diagnostic device, or by using a different catheter with diagnostic capabilities, all of which is well known to those skilled in the art. Once the site is located, one or more of the electrodes are moved to the proper location(s) and a power supply (not shown) is connected to the medical device 10 to energize one or more of the electrodes in either a constant voltage, power, or temperature mode as is well known to those skilled in the art. The electrodes can be energized simultaneously, sequentially, or in accordance with some other pattern. For example, the slidable electrode 12 can be energized and displaced relative to the shaft 14 to create a linear lesion, with a tip electrode 64 then being energized to perform any necessary follow-up burning as is well known in the art.

Often, in order to disrupt an arrhythmia, a long, continuous lesion must be formed. The medical device 10 of the present invention is designed to facilitate creating continuous lesions. The clinician simply manipulates the medical device 10 until the displaceable electrode 12 comes into contact with the patient's tissue and is located at one end (preferably the distal end) of the arrhythmia. Ablation energy, for example, RF energy, is then delivered to the electrode 12, and the electrode is left in place for an amount of time sufficient to ablate the adjacent tissue. The clinician then manipulates the displacement mechanism 20 so that the electrode travel a selected distance determined by the spacing between the detent pins 40 or detent grooves 50. In one embodiment, this is achieved by sliding the slider control member 26 relative to the control handle 24 until the engagement member engages the next detent pin or groove. Once the electrode 12 in the new location, ablation energy is again delivered to the electrode 12 so that it ablates the adjacent tissue. This procedure is repeated one or more times to create the continuous lesion, without requiring the clinician to move the catheter shaft 14 or the entire medical device 10. Subsequently, the tip electrode 64 may be used for follow-up burning as described above.

From the foregoing, it will be apparent to those skilled in the art that the present invention provides a medical device which facilitates the creation of continuous lesions, without requiring an elongated electrode that hinders the flexibility of the medical device. In addition, the medical device of the present invention provides an easily actuated mechanism for displacing an electrode to facilitate creating continuous lesions.

Having thus described preferred embodiments of the present invention, it is to be understood that the above-described arrangement and system is merely illustrative of the principles of the present invention, and that other arrangements and systems may be devised by those skilled in the art without departing from the spirit and scope of the invention as claimed below.

What is claimed is:

1. A medical device comprising:
   a control handle;
   an elongated tubular shaft;
   an electrode slidably mounted over the shaft;
   an elongated displacement member connected to the electrode; and
   a control mechanism connected to the displacement member and operative to displace the displacement member and the electrode in predetermined increments, wherein the control mechanism comprises a slider member slidably mounted on the handle, the control handle including a plurality of spaced apart engaging means and the slider member including means for releasably receiving the respective engaging means.

2. The medical device of claim 1, wherein the engaging means comprises a plurality of spaced apart detent pins, and the means for releasably receiving comprises a resilient recess formed on the slider member.

3. A medical device comprising:

a control handle;

an elongated tubular shaft;

an electrode slidably mounted over the shaft;

an elongated displacement member connected to the electrode; and a control mechanism connected to the displacement member and operative to displace the displacement member and the electrode in predetermined increments, wherein the control mechanism comprises a slider member slidably mounted on the handle, the slider member including an engaging means and the control handle including a plurality of spaced apart receiving means for releasably receiving the engaging means.

4. The medical device of claim 3, wherein the receiving means comprises a plurality of spaced apart detent grooves, and the means for releasably engaging comprises a spring loaded ball plunger.

5. A method for manipulating an electrode, comprising:

(a) positioning an electrode at a selected site within a patient, the electrode having predetermined dimensions;

(b) sensing electrical activity through the electrode;

(c) displacing the electrode a predetermined increment, wherein the predetermined increment is determined based upon one or more of the dimensions of the electrode; and (d) repeating steps (b) and (c) one or more times to sense electrical activity at different locations within the patient.

6. A medical device comprising:

a control handle;

an elongated tubular shaft;

an electrode slidably mounted over the shaft;

an elongated displacement member connected to the electrode; and a control mechanism Connected to the displacement member and operative to displace the displacement member and the electrode in predetermined increments, wherein the control mechanism comprises a slider member slidably mounted on the handle, the slider member having a first feature that contacts a plurality of spaced apart second features formed as part of the handle such that the first feature and one of the second features releasably engage one another.

7. The medical device of claim 6, wherein the first feature is a means for releasably engaging a plurality of spaced apart receiving means that comprise the second features.

8. The medical device of claim 7, wherein the first feature is a spring-loaded ball plunger and the second features comprise a plurality of spaced apart detent grooves.

9. The medical device of claim 6, wherein the second features comprise a plurality of spaced apart engaging means and the first feature is a means for receiving the respective engaging means.

10. The medical device of claim 9, wherein the second features comprise a plurality of spaced apart detent pins and the first feature comprises a resilient recess formed on the slider member.

* * * * *